United States Patent
Mogul

(10) Patent No.: US 7,182,766 B1
(45) Date of Patent: Feb. 27, 2007

(54) ADJUSTABLE OSTEOTOMY GUIDE

(76) Inventor: Stuart Mogul, 15 W. 72$^{nd}$ St., New York, NY (US) 10023

( * ) Notice: Subject to any disclaimer, the term of this patent is extended or adjusted under 35 U.S.C. 154(b) by 493 days.

(21) Appl. No.: 10/637,442

(22) Filed: Aug. 8, 2003

(51) Int. Cl.
*A61F 5/00* (2006.01)

(52) U.S. Cl. .......................................... 606/87; 606/96

(58) Field of Classification Search ............ 606/79–91, 606/96, 180, 176; 83/821–829, 522.25; 451/549
See application file for complete search history.

(56) References Cited

U.S. PATENT DOCUMENTS

| | | | |
|---|---|---|---|
| 4,409,973 A | 10/1983 | Neufeld ........................ | 128/92 |
| 5,147,364 A | 9/1992 | Comparetto .................. | 606/85 |
| 5,211,645 A | 5/1993 | Baumgart et al. ............ | 606/96 |
| 5,431,656 A | 7/1995 | Clift, Jr. et al. .............. | 606/86 |
| 5,520,692 A | 5/1996 | Ferrante ....................... | 606/80 |
| 5,569,260 A | 10/1996 | Petersen ....................... | 606/88 |
| 5,578,038 A | 11/1996 | Slocum ........................ | 606/87 |
| 5,601,565 A | 2/1997 | Huebner ....................... | 606/87 |
| 5,693,056 A | 12/1997 | Carls et al. ................... | 606/86 |
| 5,843,085 A | 12/1998 | Graser ......................... | 606/87 |
| 5,938,665 A | 8/1999 | Martin ......................... | 606/88 |
| 6,007,535 A * | 12/1999 | Rayhack et al. .............. | 606/57 |

* cited by examiner

*Primary Examiner*—Brian E. Pellegrino
(74) *Attorney, Agent, or Firm*—Goldstein Law Offices PC.

(57) ABSTRACT

An osteotomy guide having a frame and a pair of guide pins, for creating a desired cut in a bone. The frame has an outer frame, and an inner frame which is telescopically mounted within the outer frame. Both the inner frame and outer frame having open ends and a guide pin sleeve. The inner frame and outer frame together define a main slot which is adjustable in length by moving the inner frame with respect to the outer frame. The frame is mounted to the bone by creating anchoring holes in the bone and extending the guide pins through the guide pin sleeves and into the anchoring holes, such that the guide pins are parallel in all planes. A controlled cut is created by using the guide pins as a visual guide or inserting a saw blade through the main slot.

4 Claims, 4 Drawing Sheets

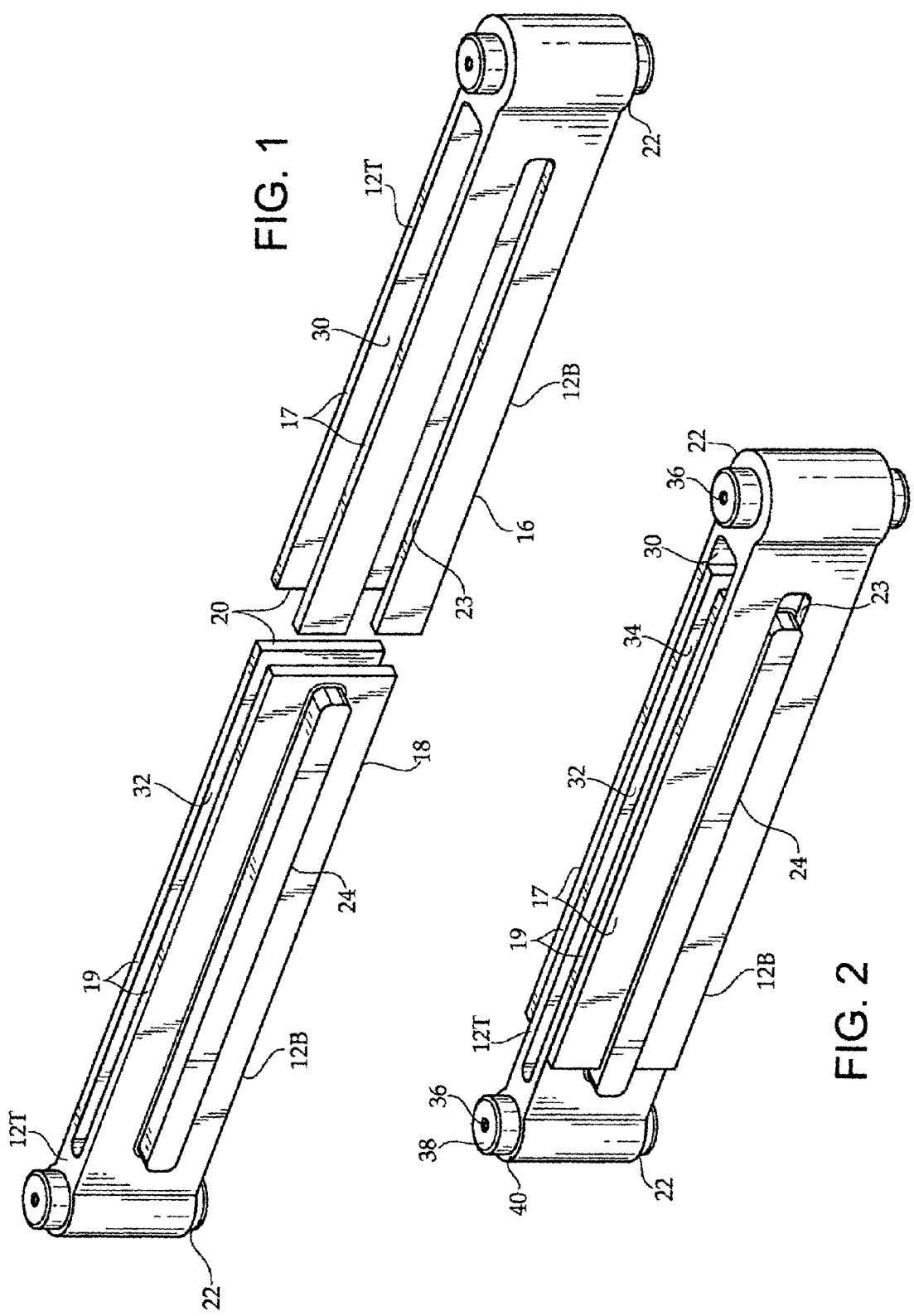

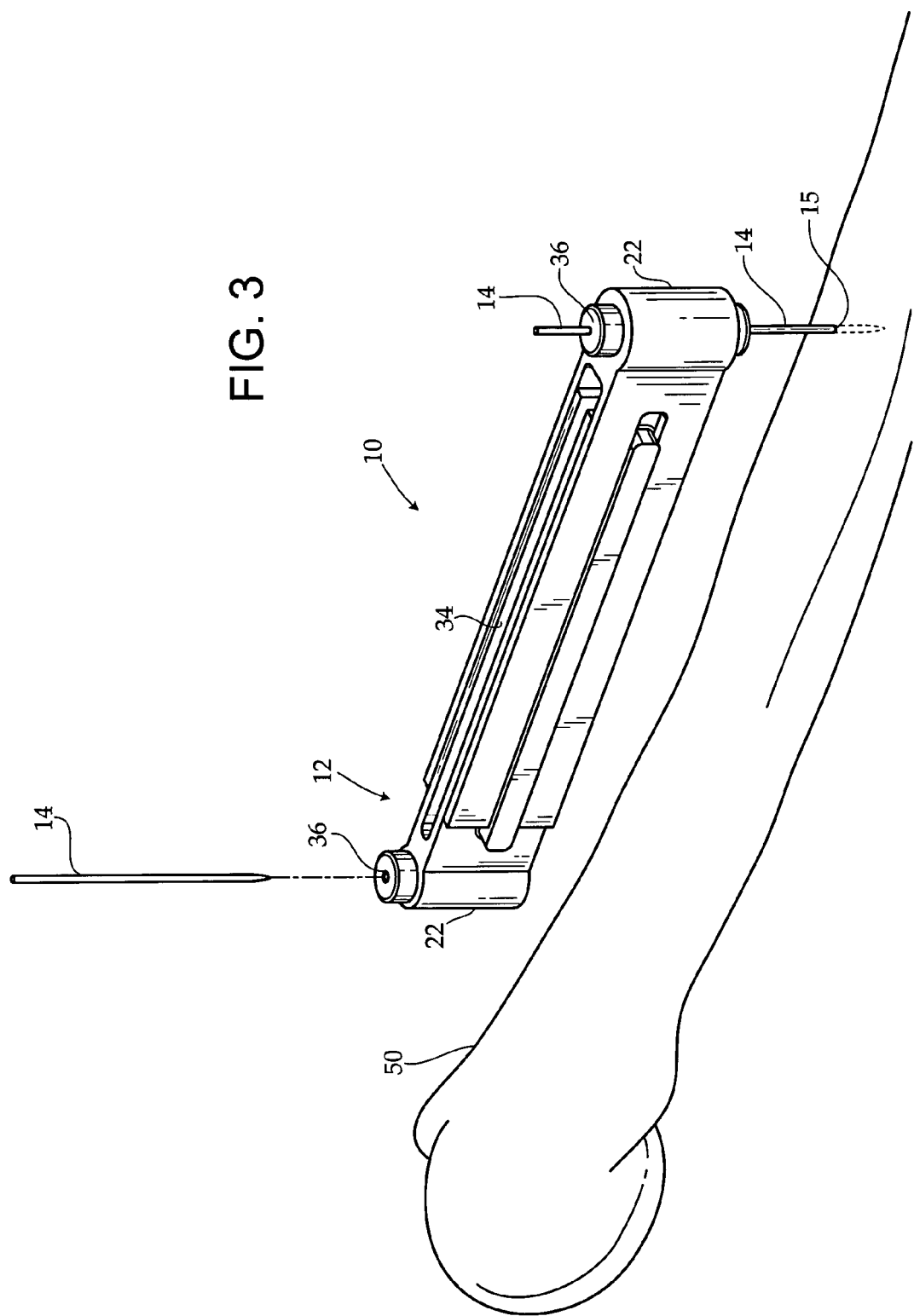

ADJUSTABLE OSTEOTOMY GUIDE

BACKGROUND OF THE INVENTION

The invention relates to an adjustable osteotomy guide. More particularly, the invention relates to a device that facilitates making controlled and parallel cuts into a bone by inserting a pair of guide pins to the bone in a parallel orientation near a desired cut and providing at least a visual guide for the operation of a saw blade in making a parallel cut.

A variety of surgical techniques require bone cutting. The success of many of these surgical techniques can rely on the precision with which a cut is made. Further, certain surgical cuts require a series of parallel cuts. However, it is often difficult for a surgeon to maintain a precise angular relationship between several cuts.

Further, often a reciprocating saw is used to make such cuts. However, considerable risks are inherent with using any powered cutting tool within the human body. At a minimum, a wandering cut can cause unnecessary trauma to surrounding tissue and can increase patient recovery time. Further, an imprecise cut can detract from the success of the surgery and thereby thwart the goals of the surgery. Still further, an uncontrolled movement can easily cause severe injury to the patient. Thus, it is highly desirable to carefully guide the saw when it is used during surgery.

Others have proposed devices that seek to guide a saw blade when within the human body. Such guides are often one sided—allowing some directional control and providing some stability. Accordingly, some of these devices will often allow relatively controlled cuts. However, many of these guides do not sufficiently restrain the saw blade to prevent mishaps, and do not provide sufficient guidance to a surgeon to allow multiple parallel cuts to be made.

U.S. Pat. No. 5,601,565 to Huebener discloses an osteotomy method and apparatus. The system of Huebener is intended for creating a transverse cut and is most suitable for use in correcting angular deformities. However, Huebener does not allow control over the length of the cut. Accordingly, Huebener is most suitable for making 'open ended' cuts, rather than cuts of a precise length bounded on both sides by bone.

U.S. Pat. No. 4,409,973 to Neufeld discloses a method and apparatus for corrective osteotomy. Neufeld uses an arcuate hand saw in proximity to a guide pin to create an arcuate cut. However, Neufeld is only suitable for making a curved cut concentric with the guide pin.

U.S. Pat. No. 5,147,364 to Comparetto discloses an osteotomy saw, which is moveable within it's own arcuate slot that is anchored to the bone. However, Comparetto does not allow for precise control of the length of the cut, and is only intended for making arcuate cuts.

While these units may be suitable for the particular purpose employed, or for general use, they would not be as suitable for the purposes of the present invention as disclosed hereafter.

SUMMARY OF THE INVENTION

It is an object of the invention to provide an osteotomy guide which provides guidance to the surgeon in producing parallel cuts. Accordingly, the guide allows a pair of pins to be properly positioned prior to insertion into the bone, wherein the pins are parallel in all planes. The pins are inserted using a frame having a pair of guide pin sleeves. Once inserted into the bone, the guide pins serve to help the surgeon produce parallel cuts by providing a point of reference for maintaining the same vertical angle during an initial and any subsequent cuts.

It is an object of the invention to produce an osteotomy guide which facilitates making straight and precisely located cuts in a bone. Accordingly, the frame of the osteotomy guide has a main slot which extends substantially between the guide pin sleeves. The saw may be operated through the main slot, wherein its cutting blade extends within the main slot. The main slot constrains transverse movement of the saw to maintain a straight cutting line at the desired location, and allows a cut to be created which is parallel to the guide pins.

It is a further object of the invention to provide an osteotomy guide which allows the longitudinal length of the cut to be precisely controlled. Accordingly, the guide comprises two telescoping frame sections, with the main slot coextensive between both frame sections, to control the distance between the guide pins when mounted in the bone and allow the user to shorten and lengthen the slot to potentially provide boundaries for the longitudinal movement of the saw on the bone when made through the main slot of the frame.

It is a still further object of the invention to provide an osteotomy guide which easily anchors to the bone in a precise location. Accordingly, once the location and length of the cut is determined, the frame is positioned over the bone and the location of anchoring holes are determined. The holes are drilled into the bone, and the frame is anchored to the bone using guide pins extending through the guide pin sleeves and into the anchoring holes. The guide pins so positioned are parallel in all planes. The frame may be removed so that the pins serve as a visual guide to the surgeon in making the cuts.

It is yet a further object of the invention to provide an osteotomy guide which allows cuts to be made at a precise angular relationship. Accordingly, the guide pins can serve to visually orient the surgeon in maintaining the parallel nature of a series of cuts. Also, additional frames may be attached to the main frame wherein the additional frames are pivotally attached to the main frame at one or more of the guide pin sleeves. The position of the additional frame with respect to the angular frame is adjusted in order to adjust the position of the main slots to prepare for primary and additional cuts at a desired angle.

The invention is an osteotomy guide having a frame and a pair of guide pins, for creating a desired cut in a bone. The frame has an outer frame, and an inner frame which is telescopically mounted within the outer frame. Both the inner frame and outer frame having open ends and a guide pin sleeve. The inner frame and outer frame together define a main slot which is adjustable in length by moving the inner frame with respect to the outer frame. The frame is mounted to the bone by creating anchoring holes in the bone and extending the guide pins through the guide pin sleeves and into the anchoring holes, such that the guide pins are parallel in all planes. A controlled cut is created by using the guide pins as a visual guide or inserting a saw blade through the main slot and constraining transverse and longitudinal movement of the saw blade within the main slot.

To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

In the drawings, like elements are depicted by like reference numerals. The drawings are briefly described as follows.

FIG. 1 is a diagrammatic perspective view of the frame of the present invention, with the frame sections separated.

FIG. 2 is a diagrammatic perspective view of the frame, per se.

FIG. 3 is a diagrammatic perspective view, illustrating the guide pins being attached into the bone in a parallel relationship using the frame.

DETAILED DESCRIPTION OF THE PREFERRED EMBODIMENTS

Figure 4:
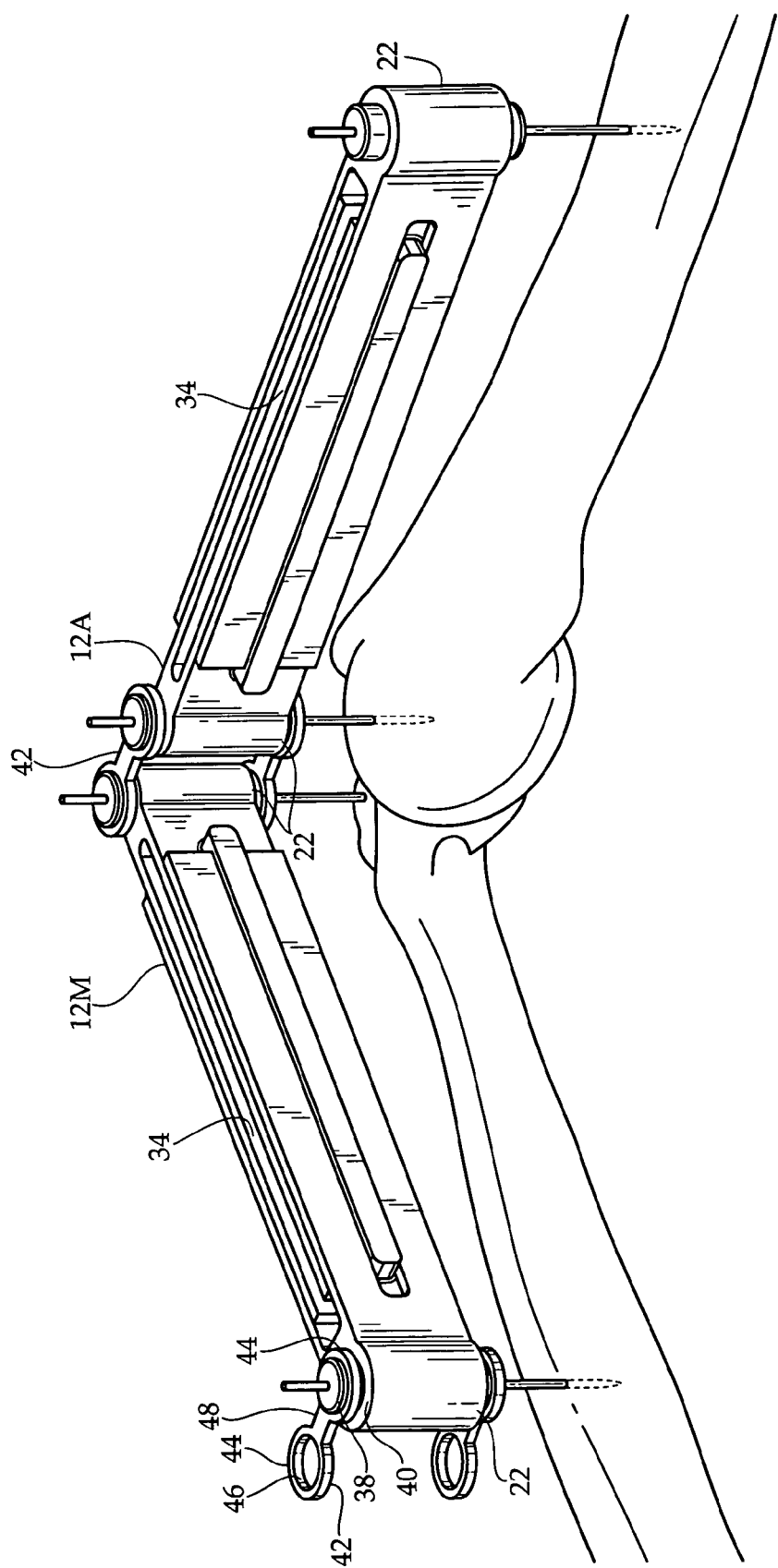
FIG. 4 is a diagrammatic perspective view, illustrating a further embodiment of the invention where an additional frame is linked to the main frame, to provide a pair of cuts on a precise angle, and where provisions are made for linking another 'additional frame' to the main frame.

FIG. 3 illustrates an osteotomy guide 10 having a frame 12, and a pair of guide pins 14. Referring to FIG. 1 and FIG. 2, the frame 12 has a pair of frame sections—namely an outer frame section 16 and an inner frame section 18. The frame sections 16, 18 each have an open end 20 and a guide pin sleeve 22 at an opposite end therefrom.

The inner frame section 18 has a pair of inner vertical panels 19, which are substantially parallel to each other and extend from the guide pin sleeve 22 to the open end 20 of the inner frame section 18. The inner frame panels 19 define an elongated inner slot 32 therebetween. The outer frame section 16 has a pair of outer vertical panels 17, which are substantially parallel to each other and extend from the guide pin sleeve 22 to the open end 20 of the outer frame section 16. The outer frame panels 17 define an elongated outer slot 30 therebetween.

The inner frame section 18 is sized to fit and telescopically slide within the outer frame section 16 such that the inner vertical panels 19 extend between and parallel to the outer vertical panels 19 within the outer slot 30. A main slot 34 is defined by the longitudinal continuance of the outer slot 30 and inner slot 32, whereby the main slot 34 is of inconsistent width but is continuous substantially between the guide pin sleeves 22.

To facilitate smooth telescopic relative movement of the inner frame section 18 within the outer frame section 16, the outer frame section has at least one horizontally and longitudinally extending side slot 23 in at least one of the outer vertical panels 17, and the inner frame section has at least one longitudinally extending lateral protrusion 24 extending from at least one of the inner vertical panels 19. The side slot 23 extends horizontally from the open end 20 of the outer frame section 16 to near the guide pin sleeve 22 thereon. The lateral protrusion 24 extends within the side slot 23 and thereby allows controlled slidable relative movement of the inner frame section 18 with respect to the outer frame section 16 and control over the distance between the guide pin sleeves 22. The inner frame section 18 and outer frame section 16 share a substantially common top surface 12T and bottom surface 12B. In a broad sense, the guide pin sleeves 22 are located on opposite ends of the frame 12.

Preferably, each outer frame section 16 has two side slots 23, such that one of the side slots 23 extends fully through each outer vertical panel 17 to the outer slot 30. In addition, each inner frame section 18 preferably has two lateral protrusions 24, wherein each inner vertical panel 19 has one of the protrusions extending laterally outward away from the inner slot 32.

The guide pin sleeves 22 extend fully from the top surface 12T to the bottom surface 12B. The guide sleeves 22 each have a guide sleeve bore 36 which extends fully from the top surface 12T to the bottom surface 12B. The guide pin sleeves 22 and the guide sleeve bores 36 are substantially parallel in all planes. The guide bores 36 are sized to closely accommodate the guide pins 14 to maintain the guide pins in a parallel relationship.

As illustrated, the guide sleeve 22 may have a compound construction, wherein a guide sleeve pivot 38 extends upward slightly above the top surface 12T of the frame, such that the top surface 12T provides a shoulder 40 on the top surface 12T around the guide sleeve pivot 38.

Referring again to FIG. 3, the guide pins 14 are being attached into the bone using the frame 12. In particular, the frame 12 may be positioned over the bone 50 at a desired cutting location where a desired cut is to be made having a desired cut length, such that the main slot 34 is aligned with the desired cut. The inner frame section 18 and outer frame section 16 may be telescopically adjusted to vary the distance between the guide pin sleeves 14 and ultimately—the guide pins 14. The frame 12 may be adjusted by telescopically sliding the inner frame section 18 with respect to the outer frame section 16, such that the guide pins sleeves 14 are suitably positioned and so that the main slot 34 is substantially the same in the length as the desired cut length. The frame 12 may be anchored to the bone by drilling anchoring holes 15, using the guide pin sleeves 22 as a template to ensure that the guide pins 14 are inserted into the bone 50 such that the guide pins 14 are parallel in all planes, and simultaneously inserting the guide pins 14 through the guide pin bores 36 into the anchoring holes 15. When the guide pins 14 are parallel in all planes, it will aid the surgeon in producing one of more parallel cuts.

In general, the frame 12 is attached to the bone 50 by inserting one of guide pins 14 through each of the two guide pin sleeves 22 and into one of the two anchoring holes 15. The guide pins is in the configuration of a wire, such as a K-wire. The K-wire is a wire which one half (½) to three quarters (¾) of a millimeter (mm) in diameter, which has a pointed diamond tip. The anchoring hole 15 is drilled and the K-wire guide pin is thereby inserted using a K-wire driver, which engages the K-wire and creates a hole using the wire while simultaneously driving the K-wire into the bone. When it is desired to remove the K-wire, the K-wire driver is once again engaged with the K-wire and the process is reversed. Accordingly, in the present context, the K-wire driver is positioned over each guide pin sleeve 22, and a K-wire is driven through the guide pin sleeve 22 into the bone 50. The guide pin sleeves 22 ensure that the K-wires are parallel. Once the guide pins 14 are inserted, the frame can be removed by simply sliding the frame upward and off of the guide pins. Then the guide pins 14 are used as a visual guide to allow the surgeon to make several parallel cuts, such that the K-wires provide the surgeon with a point of reference in the vertical planes such that the cuts can be substantially parallel in both vertical planes regardless of their positions in the horizontal plane.

Figure 5:
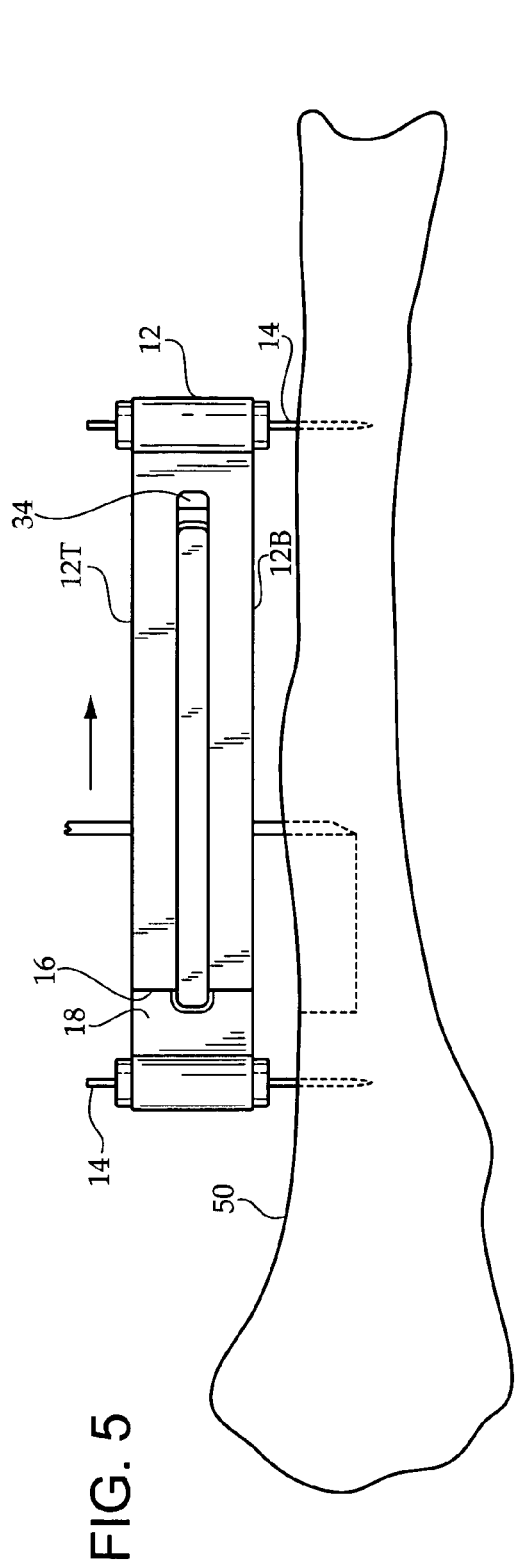
FIG. 5 and FIG. 6 are diagrammatic side elevational views, with a saw blade inserted into the slot, illustrating how a cut is controlled using the guide, and how the cut length is adjusted by telescopically adjusting the relative positions of the frame sections.
Figure 6:
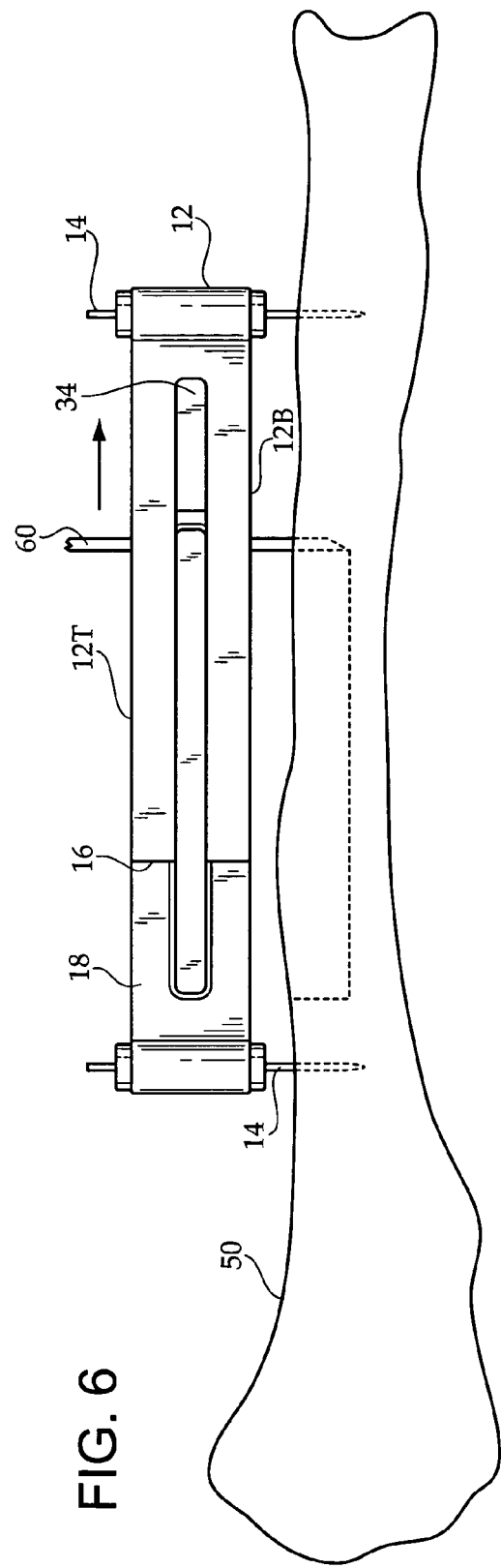

Referring to FIG. 5, the frame 12 is still attached to the bone 50 using two guide pins 14 which are longitudinally positioned along the bone 50. The frame 12 may serve as a guide to allow the bone to be cut using the main slot 34 of the frame. Accordingly, a saw blade 60 extends through the main slot 34 fully from the top 12T, past the bottom 12B, where it engages the bone 50. The saw blade 60 is allowed to move fully longitudinally within the main slot 34, substantially between the guide pin sleeves 22, and is limited in its transverse movements. The main slot 34 essentially acts as a saw blade tract, which directs and constrains the movements of the saw blade. The cut made will be parallel to the guide pins 14. Further, as shown in FIG. 6, the frame 12 may be easily adjusted by manipulating the relative positions of the inner frame section 18 and the outer frame section 16 so as to alter the length of the cut allowed.

When the frame 12 is used primarily to anchor the guide pins 14 in the bone in a parallel relationship, the cut may conveniently extend between the guide pins 14. Additional cuts may be located in other locations that are not between the guide pins 14. However, the guide pins may easily serve as a visual reference for making those cuts as well, such that the saw blade may be oriented so that it is parallel in both vertical planes by using the guide pins as a reference point.

Referring now to FIG. 4, a further embodiment of the invention is illustrated, wherein the frame as previously described and illustrated is known as a main frame 12M, and wherein an additional frame 12A having a substantially identical structure as the main frame, is pivotally attached to the main frame 12M by joining their guide pin sleeves 22 with a link 42. The link 42 as illustrated has a pair of rings 44, each having a ring hole 46, where the rings 44 are attached by a tether member 48. Accordingly, for each link 42, one of the rings 44 is extended around the one of the guide pin sleeves 22 of the main frame 12M, and the other of the rings is extended around the other of the guide pin sleeves 22 of the additional frame 12A. In particular, the rings 44 are sized to extend around the guide sleeve pivot 38, and rest upon the shoulder 40. Accordingly, once the main frame 12M is anchored to the bone, the additional frame can be pivoted with respect to one of the guide sleeves 22 of the main frame 12M, to position their main slots 34 at a desired angle, so that a primary cut can be made by the main frame, and an additional cut can be made by the additional frame at the desired angle to the primary cut.

The arrangement shown, linking the guide pin sleeves 22 using the rings 44, allows the main frame 12M and additional frame 12A to have substantially identical structure, so that they may be used interchangeably. However, if it is desired to make one of the guide pins the precise origin of the angle between prospective cuts, then the additional frame can be configured to clamp onto the guide pin sleeve 22 so that it can pivot axially around the guide pin 14 extending therein, or so that the two guide pin sleeves actually share a common guide pin 14. Such can be accomplished even by using a pair of long guide pins 14 and one short guide pin, such that one of the guide pin sleeves 22 of the additional frame 12A is 'stacked' vertically upon one of the guide pin sleeve 22 of the main frame 12M, and both are fastened to the bone using one of the long guide pins, which then serves as a common axis and the origin of the angle between prospective cuts. The other long pin would be used to anchor the non-common guide pin sleeve 22 of the additional frame 12A to the bone, and the short pin would anchor the non-common guide pin sleeve 22 of the main frame 12M to the bone.

Further, a pair of 'additional frames' 12A can be attached on opposite sides of the main frame 12M, such that each additional frame 12A is attached to one of the guide pin sleeves 22 of the main frame 12M. Such an arrangement allows for "Z" cuts to be made with the saw blade constrained by the frames during all of the cuts, to directly guide a saw blade in making parallel cuts.

In addition, the angle between the main frame and the additional frames can be fixed in position by employing set screws which protrude from at least one of the frames near its guide pin sleeve, to engage another adjacent, pivotally mounted frame, to stop the two adjacent, pivotally mounted frames from pivoting inward toward each other. Such an arrangement allows the angle to be set prior to its use with a patient.

In conclusion, herein is presented an osteotomy guide which allows a pair of guide pins to be easily anchored to a bone to extend parallel in all planes, and allows a cut to be made in the bone is a precisely controlled fashion, such that the guide pins serve as a visual guide for the surgeon to create parallel cuts in the bone and the frame can used to make one or more cuts by directly constraining the movement of the saw blade using an adjustable main slot. The invention is illustrated by example in the accompanying drawings and in the foregoing description. However, numerous variations are possible, while adhering to the principles of the present invention. Such variations are contemplated as being a part of the present invention.

What is claimed is:

1. An osteotomy guide, for use in controlling a cut by a saw blade in a bone, wherein the prospective cut has a desired location and a desired length, comprising:

a frame, having a top and a bottom, the frame having an outer frame section and an inner frame section, each of said frame sections having a guide pin sleeve and an open end opposite from the guide pin sleeve, the guide pin sleeves each have a guide pin bore extending vertically through the guide pin sleeve, the guide pin sleeves and guide pin bores are substantially parallel and vertical, wherein a distance between the guide pin sleeves can be adjusted by sliding the inner frame section within the outer frame section, wherein the outer frame section has a pair of outer panels extending between the guide pin sleeve and open end of the outer frame section and defining an elongated outer slot therebetween, the outer slot extends fully between the top and bottom, the inner frame section having a pair of inner panels extending between the guide pin sleeve and open end of the inner frame section and defining an elongated inner slot therebetween, the inner slot extending fully between the top and bottom, the inner panels extending between the outer panels of the outer frame with the inner frame panels substantially parallel to the outer frame panels so that the inner slot and outer slot form a main slot which is longitudinally continuous substantially between the two guide pins sleeves, for allowing the saw blade to extend vertically through the main slot fully from the top to the bottom such that the saw blade is constrained in both longitudinal and transverse directions by the main slot, wherein at least one of the inner frame panels has a lateral protrusion, extending substantially from the open end of the inner frame section substantially to the guide pin sleeve of the inner frame section, wherein at least one of the outer frame panels has a side slot extending from the open end of the outer frame section substantially to the guide pin sleeve of the outer frame section, and wherein the lateral protrusion extends within the side slot to direct slidable movement of the inner frame section with respect to the outer frame section; and a pair of guide pins, which selectively extend through the guide pin sleeves which direct the guide pins into the bone in a parallel relationship prior to cutting.

2. The osteotomy guide as recited in claim 1, wherein both of the inner frame panels have lateral protrusions, and wherein both of the outer frame panels have side slots which engage the lateral protrusions to facilitate smooth telescopic adjustment of the inner frame section and outer frame section.

3. An osteotomy guide, for use in controlling a cut by a saw blade in a bone, wherein the prospective cut has a desired location, comprising:

a frame, having a top and a bottom, the frame having a pair of opposite ends and a guide pin sleeve extending vertically at each of the ends, each guide pin sleeve having a guide pin sleeve bore extending vertically between the top and bottom, the frame having an elongated main slot extending fully between the top and bottom substantially between the guide pin sleeves, the main slot for accommodating a saw blade extending vertically fully through the main slot from the top of the frame past the bottom of the frame into the bone for constraining the saw blade in both transverse and longitudinal directions, wherein the frame comprises an outer frame section and an inner frame section, each of said frame sections having one of the guide pin sleeves and an open end opposite from the guide pin sleeve, the outer frame section having a pair of outer panels extending between the guide pin sleeve and open end of the outer frame section and defining an elongated outer slot therebetween, the outer slot extends fully between the top and bottom, the inner frame section having a pair of inner panels extending between the guide pin sleeve and open end of the inner frame section and defining an elongated inner slot therebetween, the inner slot extending fully between the top and bottom, the inner panels extending between the outer panels of the outer frame with the inner frame panels substantially parallel to the outer frame panels so that the inner slot and outer slot form the main slot, and wherein the main slot can be adjusted in length by sliding the inner frame section within the outer frame section, wherein at least one of the inner frame panels has a lateral protrusion, extending substantially from the open end of the inner frame section substantially to the guide pin sleeve of the inner frame section, wherein at least one of the outer frame panels has a side slot extending from the open end of the outer frame section substantially to the guide pin sleeve of the outer frame section, and wherein the lateral protrusion extends within the side slot to direct slidable movement of the inner frame section with respect to the outer frame section; and a pair of guide pins, which selectively extend vertically through the guide pin sleeves and into the bone on opposite sides of the prospective cut and attach the to the bone in a parallel relationship, such that the slot is positioned directly above the prospective cut such that the saw blade can be extended through the main slot to cut the bone.

4. The osteotomy guide as recited in claim 3, wherein both of the inner frame panels have lateral protrusions, and wherein both of the outer frame panels have side slots which engage the lateral protrusions to facilitate smooth telescopic adjustment of the inner frame section and outer frame section.

* * * * *